(12) United States Patent
McVey et al.

(10) Patent No.: US 7,901,618 B2
(45) Date of Patent: Mar. 8, 2011

(54) INTEGRATED CONTROL AND DISTRIBUTION SYSTEM FOR THE DECONTAMINATION OF LARGE VOLUME CONVOLUTED CONFIGURATION SPACES

(75) Inventors: Iain F. McVey, Lakewood, OH (US); Paul A. Wiget, Mentor, OH (US); Michael A. Centanni, Parma, OH (US); Lewis I. Schwartz, Shaker Heights, OH (US)

(73) Assignee: Steris LLC, Temecula, CA (US)

(*) Notice: Subject to any disclaimer, the term of this patent is extended or adjusted under 35 U.S.C. 154(b) by 894 days.

(21) Appl. No.: 10/593,662

(22) PCT Filed: Mar. 23, 2005

(86) PCT No.: PCT/US2005/009653
§ 371 (c)(1),
(2), (4) Date: Sep. 20, 2006

(87) PCT Pub. No.: WO2005/094909
PCT Pub. Date: Oct. 13, 2005

(65) Prior Publication Data
US 2007/0140893 A1    Jun. 21, 2007

Related U.S. Application Data

(60) Provisional application No. 60/555,462, filed on Mar. 23, 2004.

(51) Int. Cl.
*A61L 2/24* (2006.01)
*A61L 2/00* (2006.01)
*A61L 2/20* (2006.01)
*A61L 9/00* (2006.01)
*A62B 7/08* (2006.01)

(52) U.S. Cl. .......... 422/3; 422/28; 422/33; 422/124; 422/305

(58) Field of Classification Search ............ 422/3, 124, 422/28, 305, 33
See application file for complete search history.

(56) References Cited

U.S. PATENT DOCUMENTS

| | | | |
|---|---|---|---|
| 4,067,691 A * | 1/1978 | McGady et al. | 422/1 |
| 4,896,547 A | 1/1990 | Arney et al. | 73/863.81 |
| 5,399,314 A * | 3/1995 | Samuel et al. | 422/34 |
| 5,445,792 A | 8/1995 | Rickloff et al. | 422/28 |
| 5,852,229 A | 12/1998 | Josse et al. | 73/24.06 |
| 5,872,359 A | 2/1999 | Stewart et al. | 250/339.12 |

(Continued)

FOREIGN PATENT DOCUMENTS
WO  WO 02/066082 A1  8/2002

*Primary Examiner* — Sean E Conley
*Assistant Examiner* — Kevin C Joyner
(74) *Attorney, Agent, or Firm* — Fay Sharpe LLP

(57) ABSTRACT

A large convoluted space, such as a multi-story concourse of an airport is isolated and a chemical or biological agent in the concourse is deactivated. A plurality of deactivation gas sources (100) introduce a deactivation gas at multiple points along the concourse. Fans (66, 106) circulate the deactivation gas, sensors (110) sense concentrations of the deactivation gas at numerous points around the concourse and exhaust fans (66) exhaust air, spent deactivation gas, and some deactivation gas. A control processor (84) controls the generators, the circulation fans, and the exhaust fans in accordance with the gas concentrations sensed by the sensors to increase and decrease deactivation gas concentration in selected subregions of the concourse by increasing or decreasing generation, increasing or decreasing exhausting, or altering flow patterns among subregions.

28 Claims, 5 Drawing Sheets

U.S. PATENT DOCUMENTS

| | | | |
|---|---|---|---|
| 5,882,590 A | 3/1999 | Stewart et al. | 422/28 |
| 5,906,794 A | 5/1999 | Childers | 422/28 |
| 6,077,480 A | 6/2000 | Edwards et al. | 422/28 |
| 6,375,697 B2 | 4/2002 | Davies | 55/340 |
| 6,699,701 B1 * | 3/2004 | Sulakvelidze et al. | 435/235.1 |
| 6,790,249 B2 | 9/2004 | Davies | 55/340 |
| 2001/0049926 A1 | 12/2001 | Davies | 55/385.2 |
| 2003/0035754 A1 | 2/2003 | Sias et al. | 422/29 |
| 2003/0060517 A1 | 3/2003 | Tucker et al. | 516/38 |
| 2003/0143108 A1 * | 7/2003 | Wasinger | 422/28 |
| 2005/0175500 A1 * | 8/2005 | Adams et al. | 422/29 |

* cited by examiner

INTEGRATED CONTROL AND DISTRIBUTION SYSTEM FOR THE DECONTAMINATION OF LARGE VOLUME CONVOLUTED CONFIGURATION SPACES

This application claims priority to U.S. Provisional Application Ser. No. 60/555,462; filed Mar. 23, 2004.

BACKGROUND OF THE INVENTION

The present invention relates to the decontamination arts. It finds particular application in conjunction with the deactivation of biological agents and/or chemical agents in large convoluted spaces, such as public buildings.

Heretofore, gaseous sterilants, such as hydrogen peroxide vapor, have been used to sterilize the contents of sterilization chambers, the inside of isolators, or other relatively small spaces. The gaseous sterilant was typically generated external of the chamber and flowed through it either in either a closed loop or open loop system. To be sure that sterilization was achieved, chemical and biological indicators were positioned in with the sterilized items, or in corners or other areas where diminished flow of the sterilant vapor might be expected. The chemical indicators were then visually inspected to provide substantially concurrent assurance that sterilization has been achieved. The biological indicators were incubated for greater assurance that sterilization had been achieved.

The chemical indicators had the drawback that they only measured whether the desired result had been achieved after the process was complete. Because sterilization could take an extended period of time, valuable time could be lost if the process went awry, for example if the process was failing to maintain an adequate concentration of the sterilant vapor within the chamber. Accordingly, others proposed to replace or supplement the chemical indicators with parametric monitors which provided a real time indication of conditions inside the isolator. Typical parameters included temperature, humidity, pressure, and concentration of the gaseous sterilant. Because gaseous sterilant concentration sensors were relatively expensive, their use was limited, often to a single concentration sensor. The concentration sensor could be packaged like the items to be sterilized, positioned in the single location that was deemed most difficult to sterilize, or positioned at the outlet of the chamber or isolator. By monitoring the parametric conditions inside the isolator, the introduction of sterilant vapor could be controlled such that previously selected sterilization parameters were met, particularly a combination of time, temperature, and concentration.

Rather than limiting the treatment area to a relatively small sterilization chamber or isolator, it has also been proposed to expand the size of the chamber to relatively large chambers. See, for example, U.S. Pat. No. 6,077,480. As the size of the chamber was expanded, it became convenient to use multiple sources of the decontaminant vapor and multiple sensors for sensing concentration and other parametric conditions.

The larger enclosure can be as large as a room of a building, the interior of an aircraft, or a warehouse which contains items to be decontaminated. When decontaminating whole rooms and their contents or using warehouses as the decontamination chamber, the gaseous sterilant can be supplied from the exterior, possibly through the HVAC system, or from a portable vapor source that is moved into the room. Conversely, it has been proposed to use a single vapor source to decontaminate adjacent rooms.

Vapor decontaminants, such as hydrogen peroxide vapor, have been found to be effective for deactivating (render non-toxic or less toxic to humans) various chemical weapons, such as various types of nerve gas as well as for deactivating biological agents, such as pathogenic organisms.

The prior systems have been successful in large but limited to spaces that could be treated as one or a series of individual discrete environmental regions. The present application now approaches the problem of larger more convoluted interior spaces such as airport terminal concourses, office buildings with open interior architectural designs, and the like in which treatment regions flow together.

The present invention provides a new and improved decontamination technique and apparatus which overcomes the above-referenced problems and others.

SUMMARY OF THE INVENTION

In accordance with one aspect of the present invention, a method of deactivating biological and chemical agents in a large volume with a convoluted configuration is provided. The space is isolated and a deactivation gas is introduced into a plurality of subregions of the isolated space, which subregions are physically connected. The deactivation gas is circulated within each subregion and from subregion to adjoining subregions. The introduction and circulation of the deactivation gas continues until biological and chemical agents in the space are deactivated.

In accordance with another aspect of the present invention, an apparatus is provided for deactivating biological and chemical agents in a large volume space with a convoluted configuration. A means is provided for introducing a deactivation gas into a plurality of subregions of the space, which subregions are physically interconnected. A means circulates the deactivation gas within each subregion and from subregion to adjoining subregions. A means is provided for controlling the introduction and circulation of the deactivation gas until biological and chemical agents in the space are deactivated.

In accordance with another aspect of the present invention, a computer control system is provided for controlling deactivation of biological or chemical agents in a large volume space with a convoluted configuration. The computer control system includes a processor which is programmed with a plurality of routines or algorithms. One routine or algorithm causes the space to be isolated. Another routine or algorithm controls introduction of a deactivation gas into a plurality of subregions of the isolated space, which subregions are physically interconnected. Another routine or algorithm controls circulation of the deactivation gas within each subregion and from subregion to adjoining subregions. Another routine or algorithm monitors deactivation gas concentrations at a multiplicity of locations around the isolated space. Another routine or algorithm controls exhaust fans.

One advantage of the present invention resides in its ability to decontaminate large, convoluted spaces.

Another advantage of the present invention is that it can be implemented quickly.

Another advantage resides in its automated application which enables it to be employed by operators without extensive training and skill in the decontamination arts.

Another advantage of the present invention is that it can accommodate building interiors with a large variety of different configurations.

Another advantage resides in optimization of decontaminant gas distribution and minimization of energy and reagents.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1A:
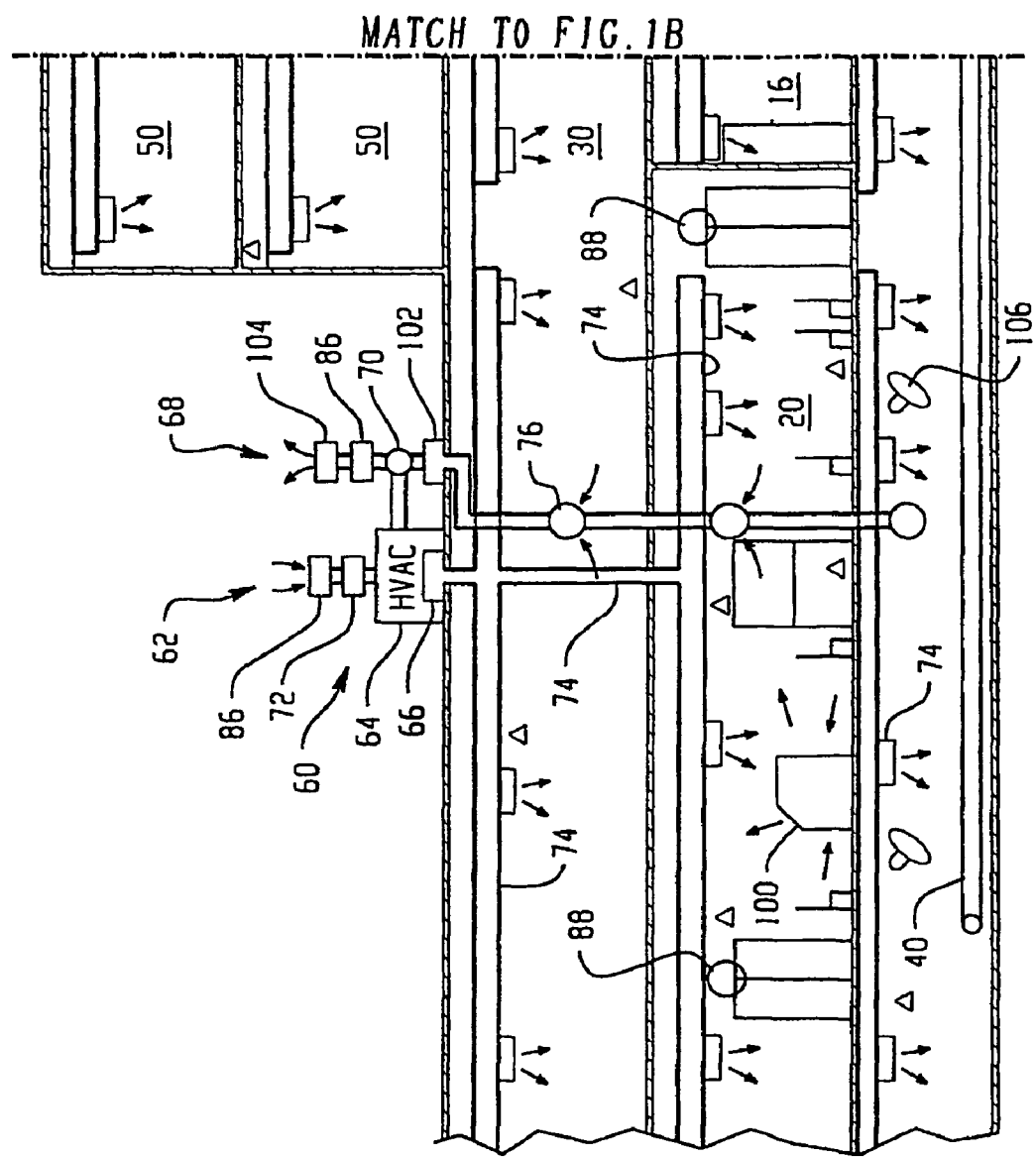
FIG. 1 is an exemplary view through a vertical section through multiple stories of the airport concourse.
Figure 1B:
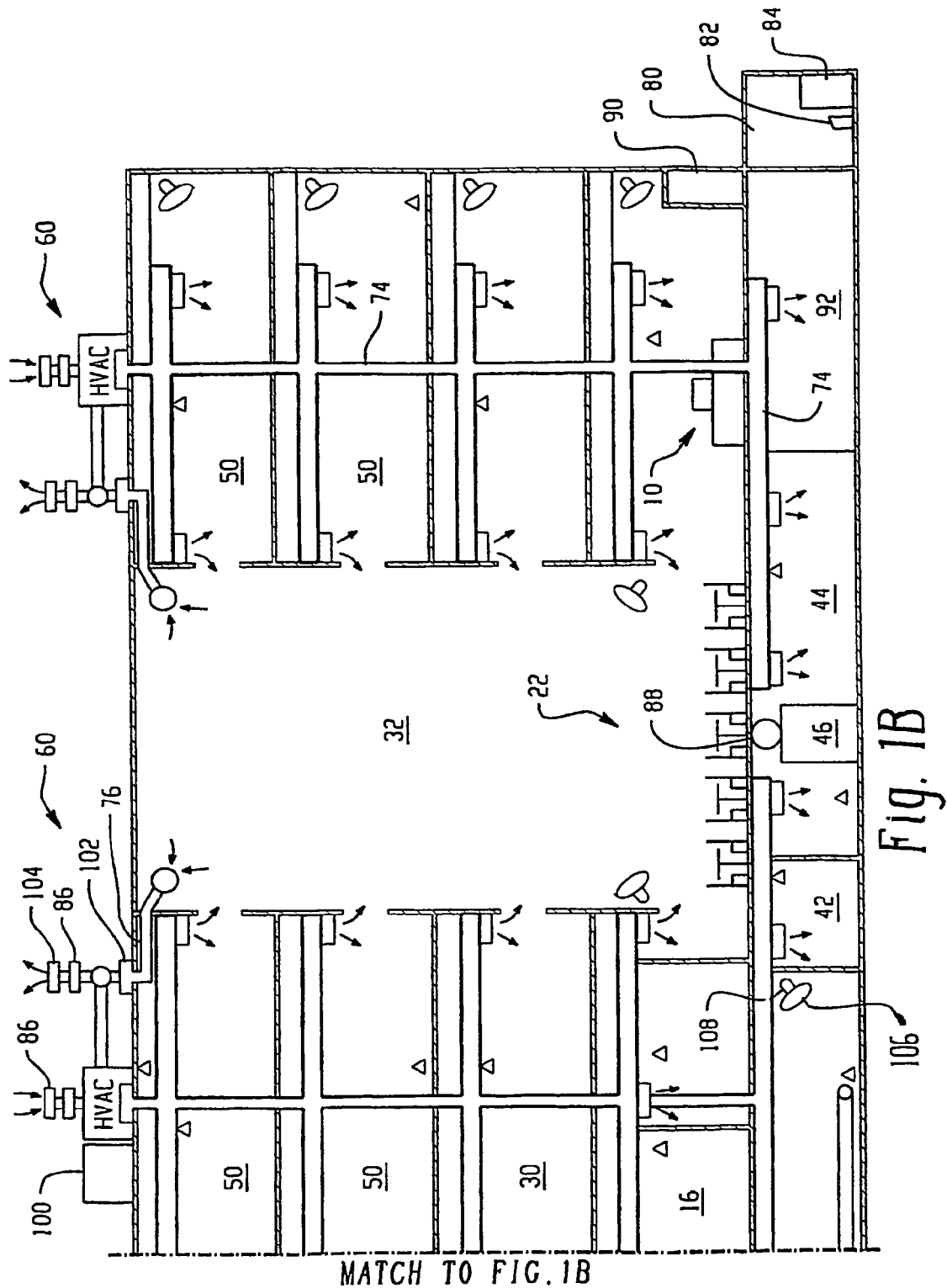
Figure 2:
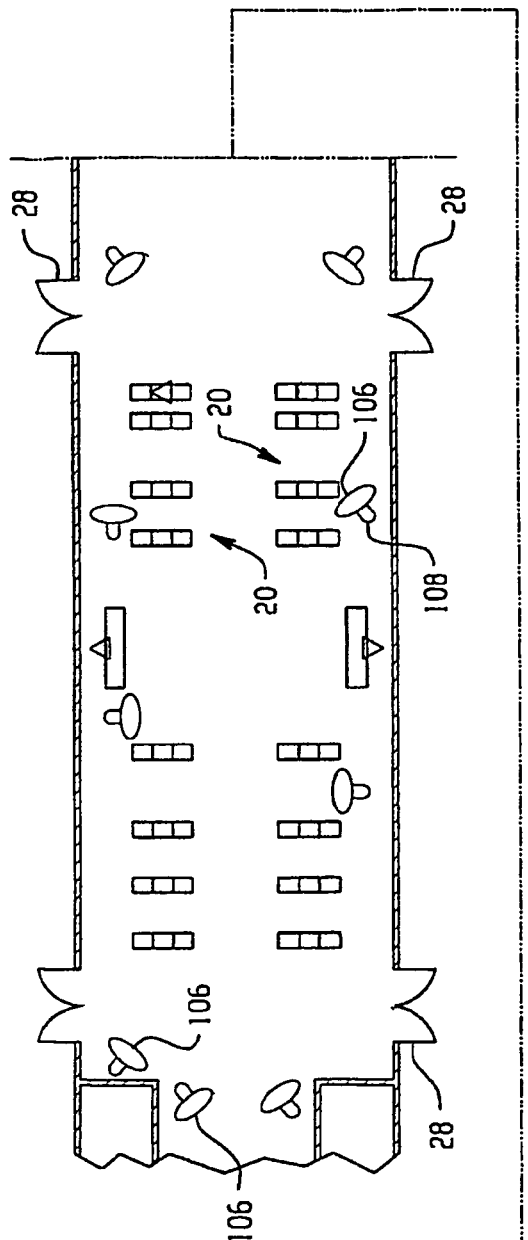
FIG. 2 is a floor plan of an exemplary open space, particularly of a portion of a single floor of an airport concourse.
Figure 2:
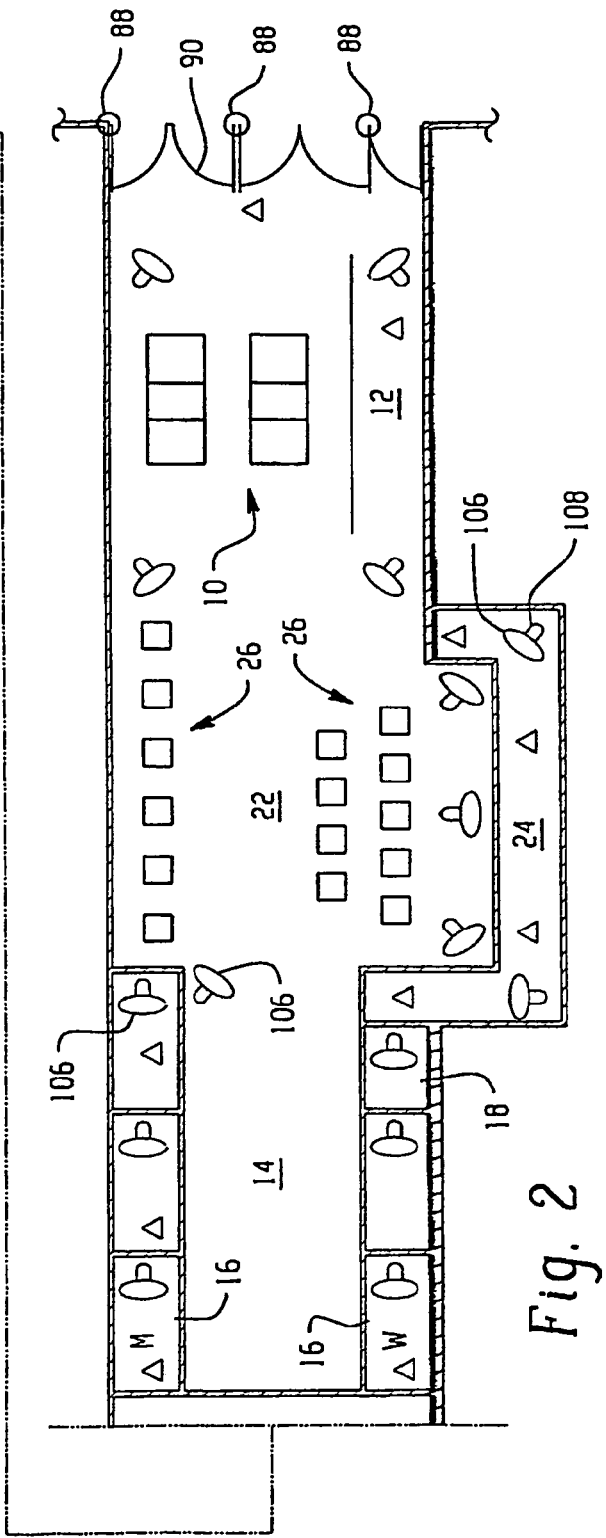

With reference to FIGS. 1 and 2, a public building, such as an airport, is divisible into isolatable zones. Ideally, the zones are relatively small. However, in practice with current airport designs, one zone might include an entire concourse due to multi-story atriums, open stairwells, the routing of HVAC systems, access passages for HVAC, plumbing, and other mechanicals, baggage handling systems, and the like. Many other existing buildings are not readily amenable to being isolated into zones of an ideally small size.

Airports typically have publicly accessed areas, such as food courts, concession areas, gates for departing flights, gates and concourses for passengers disembarking from international flights, and the like. Further, concourses typically have areas which are closed to the public, such as baggage handling systems for delivering baggage to and from the aircraft, service and maintenance facilities, storage areas for inventory for concessionaires, airlines, and the like, mechanical areas for HVAC, water heaters, and the like, trash removal facilities, office space, employee lounges, and the like.

Looking specifically to the exemplary concourse embodiment of FIGS. 1 and 2, and airport concourse of the disembarking passenger level typically includes a passenger screening area 10 where carry on items are screened and an exit passageway 12 where disembarking passengers can leave the concourse and return to the main terminal. The concourse typically includes one or more long corridors 14 from which passengers can access restrooms 16, concessionaires 18, and waiting areas 20 adjacent each gate. In some instances, the concourse also includes a food court 22 which includes a series of food and beverage vendors 24 and a seating area 26 with tables, chairs, and the like. Each gate area typically includes a jetway 28 or other departure portal which connects departing passengers and passengers arriving on domestic flights between the terminal and the aircraft.

Particularly in international airports, walkways 30 are provided on a different floor from the main concourse along which arriving passengers move on their way to customs. For openness, atriums 32 are often provided between the departing passenger concourse and the arriving international passenger concourse.

In addition to the public spaces, a concourse commonly includes areas to which passengers commonly do not have access. For example, on a lower floor, there are often conveyors 40 for conveying luggage from the luggage check-in point to the various gates, or from the various gates to the luggage pick-up region. The various concessionaires typically have storage space 42 for storing wares. Further, there is typically a garbage removal facility 44 such as corridors or conveyors along which trash from the concessionaires, the food court, and the like are conveyed for removal. There are typically portals 46 through which the luggage can be discharged or received, from which trash can be removed, at which new inventory can be received, through which airport employees can move, through which repair and replacement parts for the building mechanicals can be received, and the like. Further, the concourse may include additional levels where offices 50 and other rooms and space for the conducting of airport business are maintained. At a modern airport, a single concourse, is typically on the order of 1,000,000 cubic meters or more.

There are typically a plurality of HVAC systems 60, each of which includes a fresh air inlet 62, a heating/cooling unit 64, circulation fans 66, and an exhaust port 68. There is typically a diverter valve 70 which returns a selectable fraction of the recirculated air to the heating and cooling unit 64 and allows a preselected portion to be discharged through the discharge port 70. One or more filters 72 filter new air entering the system and recirculated air.

In a large elongated space such as an airport concourse, each HVAC system typically treats the air in a generally vertical column through the multiple stories of the building. That is, filtered and heated air is fed through supply ducts 74 to each of the floors over a limited longitudinal length of the building. Analogously, return ducts 76 are connected with return registers on each of the floors. Although each of the HVAC units treats air in a limited region of each floor, there is no isolation between each of the HVAC zones. Rather, there is a free exchange of air and air flow along the corridors.

In the event of a terrorist attack which introduces a biological toxin, such as anthrax, or a chemical agent into any part of an airport, the contaminated zone, the smallest of which is the entire concourse in the present illustrated example, is immediately sealed from the environment and the rest of the airport. To this end, an operator control station 80 includes an operator input 82 through which the operator causes a computer 84 to initiate a hermetic sealing operation to seal the zone from the environment. Specifically, the computer would immediately shut down each of the HVAC systems 60 to stop the further circulation and movement of the biological or chemical agent. Hermetic seals 86 at the air input and output to the HVAC systems are closed automatically by the computer to prevent the biological or chemical agent from being discharged to the environment. For safety, each of the portals to the jetways 28 and the portals 46 for receiving and discharging luggage, receiving inventory for the concessionaires, and other materials, for discharging garbage and the like, typically have closures. Preferably, the existing closures are reconfigured to form a hermetic seal whenever they are closed. Moreover, each of the closures is preferably equipped with an automatic door closure 88 which is actuated by the computer 84 to automatically close any of the door(s) which is open and to prevent any of the door(s) which is already closed from being opened.

The main passenger entrances and exits from the concourse are similarly equipped with hermetically sealable doors 90 which are typically in their open position. Automatic door closures 88 are again controlled by the computer 84 to close these doors and seal these portals. Preferably, in the employee access only region of the concourse, a human decontamination facility 92 is provided. This facility includes shower facilities with waste water containment that are used by passengers and personnel to remove any biological or chemical agents which they may carry on their skin, in their hair, or the like. These showers may also apply a deactivation agent appropriate to the chemical or biological agent, but which is also non-harmful to humans. Sterilization or decontamination equipment is preferably also provided for deactivating personal items of the passengers or personnel. Double seal hermetic doors are provided to enable people who have been potentially contaminated with the biological or chemical agent to move through this facility from the potentially contaminated interior of the sealed zone to the environment at large after decontamination without carrying biological or chemical agents with them.

Once all personnel have been removed from the zone, the next step is to deactivate the biological or chemical material within the zone. To this end, a vapor deactivation agent gas is introduced into the zone and maintained at adequate concentrations for an adequate time to deactivate the biological or chemical agent. In the following example, hydrogen peroxide vapor is used as the deactivation gas. However, other deactivation gases as may be appropriate to the contamination are also contemplated. Contemplated deactivation gases include ozone, vaporized hypochlorites, vaporized peracids, and other gaseous sterilants and deactivation agents.

A plurality of deactivation gas sources 100 is provided to treat different portions of the zone. The sources can take various forms such as compressed gas sources, vaporizers, reaction vessels, and the like. First, the sources may be portable sources which are brought into and positioned at various locations around the zone by attendants wearing HAZMAT suits. Alternately, a plurality of deactivation gas systems can be built into the building. For example, a hydrogen peroxide vaporizer, circulating fan, and appropriate ductwork can be building into the ceiling areas of the building, housed in the storage or mechanicals areas, or other areas which are out of sight from the passengers and are preferably inaccessible to unauthorized service personnel. The individual units may each include a source of hydrogen peroxide or other deactivation agent in liquid form. Alternately, permanent plumbing extends from each of the vaporizers to a central source of the hydrogen peroxide or other liquid which can preferably be refilled from outside of the sealed zone. As a third alternative, the gaseous deactivation agent sources can be connected with the HVAC systems such that the treated air supply ducts 74 and deliver the deactivation gas into the zone using one of the recirculation fans 66. Each of the gas sources again preferably includes a vaporizer and a source of the deactivation agent in liquid form, which sources are again preferably refillable from outside of the zone. The air to carry the gas may come through the inlet port 62, preferably through a HEPA filter or other filter which is appropriate to prevent the escape of the biological or chemical agent. Alternately, the carrier air may be supplied through the return ducts 76.

In order to increase the assurance that the biological or chemical agent will not escape to the atmosphere, it is advantageous to maintain the building at a negative pressure relative to the surrounding environment. Adding the gaseous deactivation agent will tend to increase pressure inside the zone. Moreover, if exterior air is used as a carrier for the gaseous decontamination agent, facilities for the removal of excess air are important. Further, as the deactivation agent reacts with the biological or chemical agent, additional deactivation gas is supplied to maintain the selected concentration. Again, the exhaust ports may be dedicated, built-in ports, temporary ports which are cut into walls or windows of the zone or anchored in one of the portals, or can be associated with the return duct 76 and the discharge port 68. In any instance, the discharge port includes a circulation fan 102 for drawing out the interior air and an appropriate trap 104 for assuring that the biological or chemical agent does not escape to the atmosphere with the discharged air. Further, if the deactivation gas is toxic, the trap also deactivates the deactivation gas. In the case of a biological agent such as anthrax spores and a vapor hydrogen peroxide deactivation gas, the trap may be a HEPA filter. Hydrogen peroxide vapor breaks down into oxygen and water rapidly on exposure to sunlight, and thus is normally safe for discharge directly into the atmosphere. For biological or chemical agents that cannot be filtered mechanically from the air, it may be more appropriate to draw the exhaust air through a reservoir of concentrated deactivation agent.

Maintaining the concentration of the deactivation gas in a preselected range in every region of the zone is an awkward and difficult problem. First, the zone has relatively large open areas such as adjacent the departure gates, relatively narrow corridors such as between the restrooms or concessionaires, partially isolated regions such as restrooms, more isolated but not hermetically sealed regions such as service areas and storage rooms, and the like. Moreover, many of these regions have nooks and crannies. To help distribute and circulate the deactivation gas within the regions, a plurality of fans or blowers 106 are provided. These fans or blowers again can be permanent installations, e.g., mounted to the ceilings, or may be portable devices brought in and positioned appropriately after a contamination event occurs. The fans are typically positionable to direct and circulate the deactivation gas into corners, around bends in corridors, through narrow spaces, into restrooms, under the seating at the gate areas, and other regions into which the gaseous deactivation agent may be less prone to circulate. Ideally, each of the fans includes a servo motor 108 with which the computer 84 controls the direction in which the fan is facing. The computer preferably also controls the speed of the fan and can reverse the fan.

As another complicating factor, different areas of the zone are likely to be more or less absorptive of the deactivation agent. For example, the waiting areas typically include cloth and absorptive materials in carpeting, the seating, and the like. Restrooms and the food court area include paper products including napkins, plates, towels, and the like. In the food court area, or even in trash receptacles throughout the zone, there may be food products which are more absorptive or reactive with the deactivation gas. Other zones may include only gas, ceramic, hard plastic, and other surfaces which are relatively non-absorptive of the deactivation gas. If the HVAC is used for gas delivery, some areas such as storerooms may be under served. Similarly, the HVAC delivery and exhaust may be out of balance, have dead zones, and the like. These and other differences can lead to differences in decontaminant gas concentration in different parts of the zone. These differences can be equalized by increasing the supply of the deactivation gas, redirecting the fans, and by increasing or decreasing the exhaust rate at various points within the zone.

The deactivation is typically not only concentration sensitive, but also temperature sensitive. Further, with hydrogen peroxide vapor and some other gaseous deactivation agents, it is desirable to prevent condensation of the vapor. Condensation of the gas into a liquid can have adverse effects on electrical circuitry, particularly on the electrical circuitry of electronic components such as computers, cash registers, television monitors, and the like. Condensation tends to occur at saturation which is concentration and temperature dependent, as well as pressure dependent.

In order to monitor these conditions, a large number of sensors 110 are mounted around the isolated zone, preferably at corners, in storerooms, under seats, in light fixtures, in trash receptacles, within the HVAC ducts, in the space above a suspended ceiling, in dead spaces behind signage, and other areas where there is apt to be relatively poor circulation of the deactivation gas. The sensors can be a series of portable sensors which are brought in and positioned by workers in HAZMAT suits after an incident, may be permanently mounted, or may be a combination of the two. Sensors installed at the time of an incident preferably communicate with the computer 84 via telemetry, for simplicity of installation. Permanently mounted sensors may communicate by telemetry, over dedicated communication wires, multiplexed over a data collection bus, or the like. Preferably, sensors in difficult to reach areas are preferably permanently mounted.

Due to the large number of sensors, the sensors are preferably of a low cost, readily mass manufactured nature. More preferably, the sensors include a solid-state element whose characteristics change with a concentration of the gaseous deactivation agent. Each sensor also preferably includes a temperature sensor for monitoring temperature at the sensor location for the dual purposes of use by the control computer 84 and in correcting temperature dependent variations in the output of the solid-state sensor.

Figure 3:
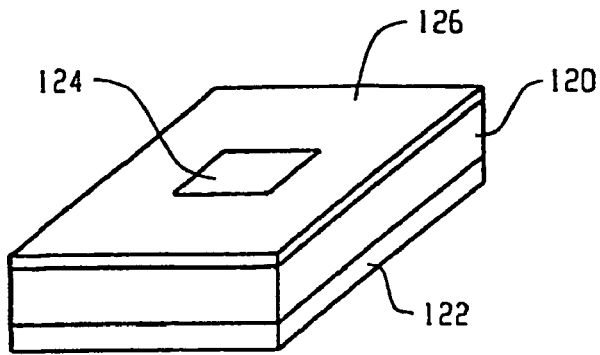
FIG. 3 illustrates an exemplary piezoelectric concentration sensor.

With reference to FIG. 3, in one embodiment, the sensor is a thin layer 120 of piezoelectric material, such as quartz, which has a thickness that causes it to oscillate at a characteristic resonance frequency. The crystal has one electrode 122 on one face and a second electrode 124 mounted on an opposite face. Preferably, at least one of the electrodes is relatively small compared to its associated crystal face such that a significant portion of at least one of the crystal faces is coated with a thin, e.g., vapor deposited, layer 126 of a resonance frequency modifying material. In the example of a hydrogen peroxide vapor as the deactivation agent, the resonance frequency altering material of layer 126 is a material that is sensitive to hydrogen peroxide, which is commonly present in conjunction with the hydrogen peroxide vapor. Preferably, the thin layer absorbs and desorbs the hydrogen peroxide as the concentration varies. A suitable layer is lead dioxide ($PbO_2$). Other metal oxides such as silver (II) oxide (AgO) or manganese (IV) oxide ($MnO_2$), metal oxides that are a mixture of single and divalent oxide states, or metal oxides having mixed valent states are also contemplated.

Alternately, the coating layer can interact with the hydrogen peroxide or other deactivation agent with a permanent reaction. In this embodiment, the oscillation frequency changes continuously in the presence of the deactivation gas, with the rate of change indicative of the current concentration. The frequency modifying layer 126 may rely on other physical or chemical properties to modify the resonance frequency. For example, the modifying layer can have physical surface properties that permit match hydrogen peroxide molecules to rest on the surface, but not water molecules, for example a catalyst type crystalline material whose crystal structure matches the peroxide molecule but not water molecules.

Figure 4:
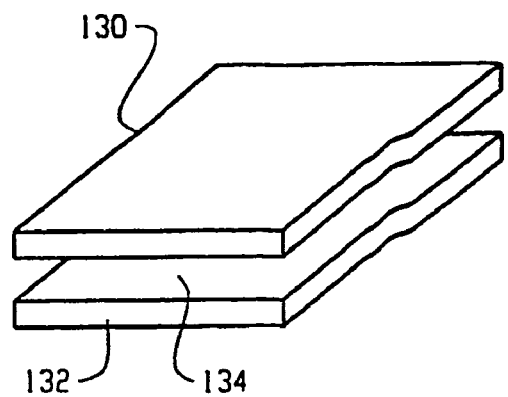
FIG. 4 illustrates an exemplary capacitive concentration sensor.

With reference to FIG. 4, another sensor embodiment includes a capacitor defined by a pair of capacitive plates 130, 132 which define a thin gap 134 therebetween. The deactivation gas flows through the thin gap 134 and with other gases in the zone functions as the dielectric between the plates. Polarizable dipole moments under an electric field alter the dielectric constant of the substance in the thin gap. In this manner, the deactivation gas, along with other polarizable dipoles in the air, defines the dielectric constant of the capacitor, hence the capacitance, varies with the relative concentration of the deactivation agent in the air. Alternately, the capacitive embodiment may use a dielectric, which is not the deactivation agent itself, but whose dielectric properties are modified by the deactivation gas by chemical interaction, physical interaction such as absorption, or the like.

Changes in capacitance can be determined in various ways, such as nulling a bridge circuit. Alternately, the capacitor can be connected with an inductance to define a resonance circuit whose resonance frequency varies with the capacitance of the capacitor, hence the concentration of the deactivation gas in the region between the plates. For temperature compensation, the sensor can include a like capacitor and inductor combination, but in which the dielectric in the gap between the capacitive plates fixed and unaffected by the decontamination agent gas. The frequency of the second resonance circuit will thus vary with temperature, but not the concentration of the decontamination agent in the air. If the frequencies of the two inductive circuits are relatively close, the signals can be combined to emphasize very small frequency shifts. A similar reference oscillator can be used for temperature compensation in the first sensor embodiment. Further, temperature compensation can come from other sources, such as a simple thermocouple.

Figure 5:
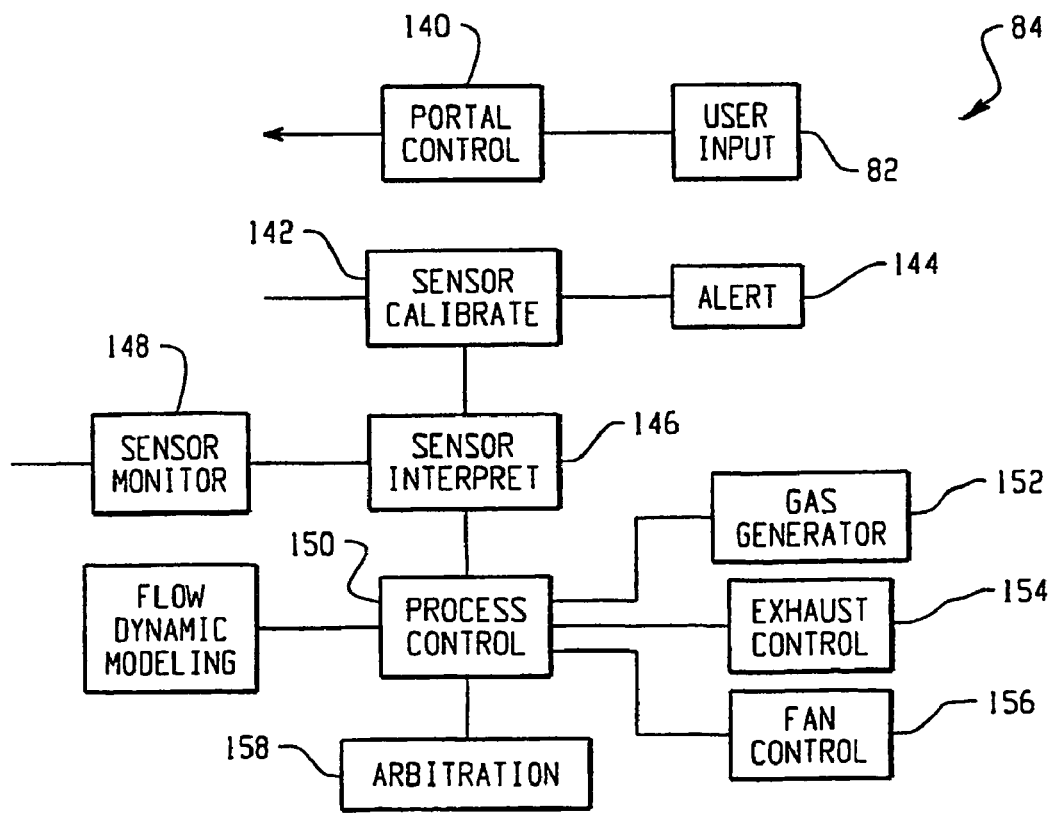
FIG. 5 is a diagrammatic illustration of a process control software system; and, FIG. 6 is a floor layout of an exemplary wing of a research building.

With reference to FIG. 5, the control computer 84 includes a portal control algorithm or routine 140 which responds to the user input 82 to close and lock all of the portals isolating the zone. The portal control routine or program further enables selective ones of the portals to be opened as may be appropriate to the decontamination process. The control computer further includes a sensor calibration routine 142 which periodically monitors all permanently mounted sensors to monitor changes in their output signal due to aging or other environmental factors when the system is not in use. The sensor calibration routine 142 produces an alert or warning output 144 if one of the sensors goes bad or out of calibration. The sensor calibration routine updates a sensor interpretation routine or look-up table 146 that is used in interpreting the output signals of each of the sensors when sensed by a sensor monitoring routine 148 during a deactivation process. A process control routine or algorithm 150 controls a generator control routine or algorithm 152 which controls the rate at which each of the decontamination gas sources generates or supplies decontamination gas, an exhaust control routine or algorithm 154 which controls the rate of each of the exhaust fans 102, removes air, and a fan control algorithm or routine 156 which controls the servo motors 108, speed, and direction of the fans 106.

In one embodiment, the process controller 150 divides the isolated zone up into subregions, with each subregion including a deactivating gas source, an exhaust port, a plurality of fans, and a plurality of sensors. The process generator then controls each of these subregions independently. Of course, each of the subregions interact which will create instances when the attempted control of neighboring regions will be conflicting. To this end, an arbitration routine 158 arbitrates and balances attempts to control the generator, exhaust fan, or circulation fans of neighboring zones inconsistently.

In another embodiment, the process controller accounts for the interaction among adjoining zones using a flow dynamic modeling routine or algorithm 160 which provides for more interactive control of adjoining and even distant subzones. For example, if the sensors in one subzone sense that the concentration of the deactivation agent is approaching the saturation level or condensation point, the process control routine 156 could lower the rate at which the corresponding source supplies deactivation gas to that subregion and/or increase the speed of the nearest exhaust fans. Alternately, the exhaust rates of neighboring subregions can be increased while the exhaust rate within the nearing saturation region is reduced such that the excess deactivation gas is drawn from the overly concentrated subregion to adjoining subregions. The fans 106 can be redirected to increase the rate of flow to neighboring regions.

In another example, instead of individual exhaust locations, there could be a single large exhaust at one end of the concourse. This would create a dynamic, unidirectional flow situation similar to a river where actions upstream affect concentrations downstream. Analogously, if a smaller number of exhaust ports are provided, then smaller flow sections are defined, at least some of which can be caused to flow in either direction, as well as at varying rates. By using conventional flow dynamic analysis algorithms 160, the process control algorithm or routine 150 can take into account interactions among different subregions of the large hermetically sealed zone.

As another example, if one subzone has too low a concentration, one might increase the rate at which deactivation gas is supplied and the rate at which the corresponding exhaust exhausts. Alternately, one could decrease the exhaust rate at that low concentration subzone and increase the rate of generation at neighboring zones. The circulation fans could be redirected to accelerate the dispersal of higher concentrations of decontamination gas from the neighboring subzones to the subzone with the low concentration.

Figure 6:
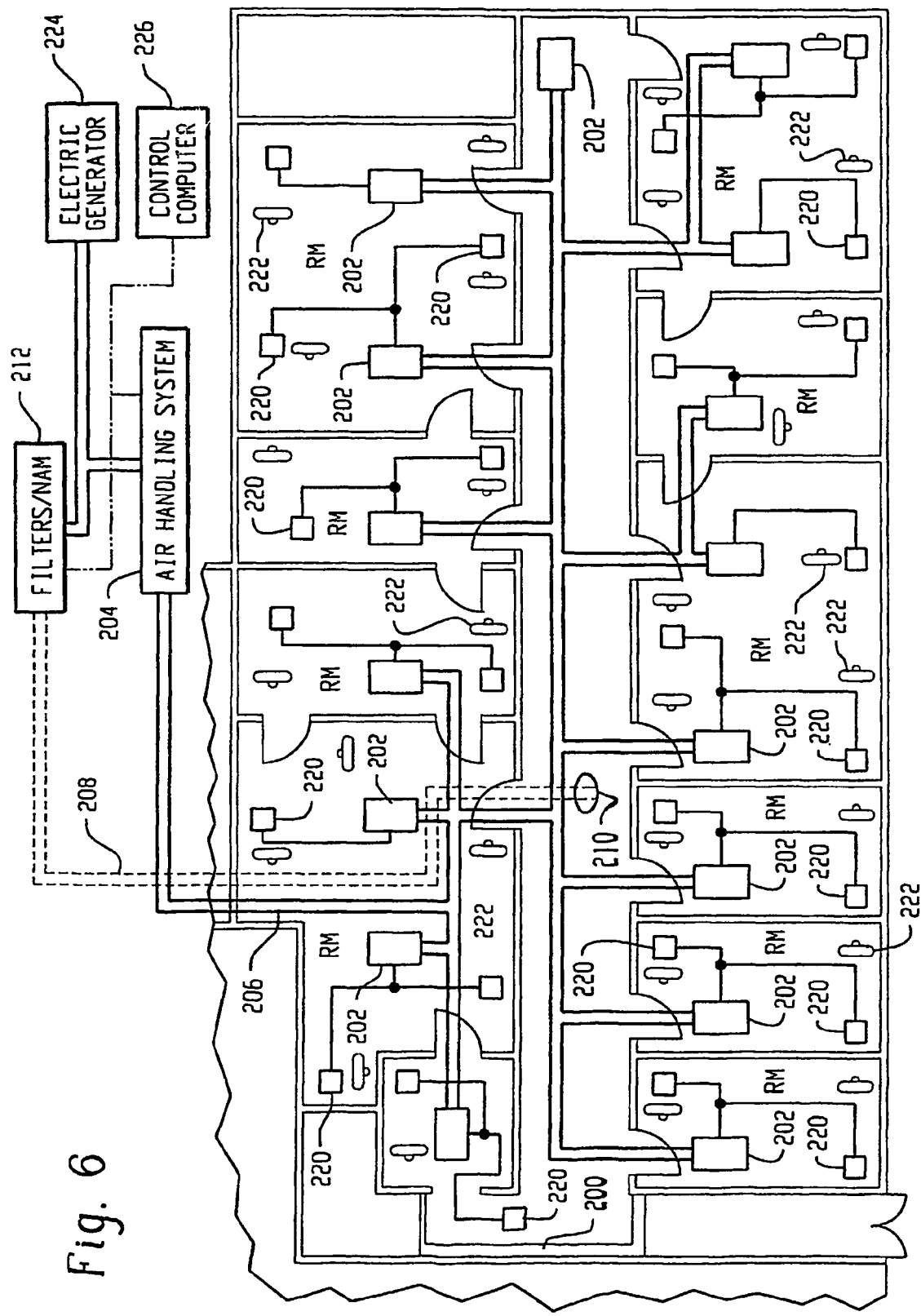

With reference to FIG. 6, the zone which is to be hermetically sealed is a wing of a building which includes a corridor, open areas with cubicles, laboratories, and individually defined offices. A means 200, such as automatic closers and sealed doors, are provided at the entrance to the wing to seal it from the rest of the building. A plurality of deactivation gas sources 202 are permanently mounted in the wing. More specifically to the preferred embodiment, at least one hydrogen peroxide generator 202 is mounted in conjunction with each room space. Large rooms, such as rooms that hold cubicles or laboratories with a plurality of laboratory stations include a plurality of generators per room. An air handling system 204 provides filtered air through feed ducts 206 to each of the hydrogen peroxide generators. An exhaust duct 208 draws gas from a single, generally centrally located exhaust inlet 210 and pumps the exhaust air through a contaminant trap 212, such as HEPA filters or other means for physically separating the contamination from the air or through a means for chemically deactivating any of the biological or chemical agent in the exhaust air.

One or more sensors 220 for sensing sterilant vapor concentration, temperature, and other parameters of concern are mounted in each room. The sensors are preferably mounted in locations which are predicted to have relatively poor air circulation or which otherwise represent areas which are anticipated to be regions that will be most difficult to deactivate. Similarly, one or more fans 222 are mounted in each room. The fans are directed to distribute and circulate the deactivation gas throughout the room, particularly into the areas that are anticipated to have poor circulation. The fans may be aimed in a common circumferential direction to create an air flow pattern in preselected direction, e.g., clockwise, around each room area. Alternately, the fans can oscillate to create turbulent air flow patterns. In the connecting corridor, deactivation gas escaping each of the rooms will flow along the corridor toward the exit port 200. Additional fans may be placed in the hall to assist this migration. Additional sensors can also be placed in the hall to monitor concentrations there. Preferably, sensors are also placed outside of the isolated zone to assure that the deactivation gas is not leaking.

An electrical generator system 224 supplies electrical power to each of the generators 202 and fans 222, and the fans in the air handling system 204. Preferably, the electrical power wires run along the air feed ducts 206 to each of the vapor generators 202. Power is redistributed from each of the generators to the fans and sensors within the same region. Preferably, communication lines also run along the feed ducts to a central control computer 226. The central control computer receives the outputs of the sensors and controls the air handling system, each of the vapor generators, and the fans accordingly. Alternately, the control functions can be distributed such that each deactivation gas generator is controlled by input from closely adjacent sensors. In rooms or other subregions that have a larger amount of deactivation gas absorptive materials or deactivation gas reactive materials, the generators will have a high duty cycle. Conversely, in rooms or regions with substantially no absorptive or reactive materials, the generators need only a very low duty cycle to maintain the deactivation effective concentrations within that region. Once reaching the initial deactivation concentrations, these low duty cycle generators may be OFF for extended periods of time.

In both described building embodiments, after the deactivation of the isolated zone has been completed, an aeration cycle is commenced to remove the deactivation gas. Introduction of the deactivation gas into the isolated zone is terminated. Thereafter, filtered air is circulated by the air handling system through the zone to flush the deactivation gas out and aerate the region. Where the deactivation gas is hydrogen peroxide vapor, the air handling system preferably includes a dehumidifier such that the supplied aeration gas (air) has minimal humidity.

Having thus described the preferred embodiments, the invention is now claimed to be:

1. A method of deactivating biological or chemical agents in a large volume space with a convoluted configuration, the method comprising:

isolating the space;

introducing a deactivation gas concurrently into each of a plurality of subregions of the isolated space, which subregions are interconnected and open to each other in such a manner that air flows between the subregions;

circulating the deactivation gas within each subregion;

circulating the deactivation gas from a subregion to its adjoining subregions;

sensing concentrations of the deactivation gas at a plurality of points around the isolated space;

based on the sensed concentrations, with a computer processor controlling the introducing of the deactivation gas, and the circulating of the deactivation gas from subregion to adjoining subregion using flow dynamics modeling such that the deactivation gas concentration in each of the subregions is maintained above a preselected minimum concentration and below a preselected maximum concentration including:

in response to sensing that the concentration of deactivation gas in one of the subregions is approaching a saturation level or condensation point, increasing the circulation of the deactivation gas from the corresponding subregion to neighboring regions, and in response to sensing that the concentration of decontamination gas in one of the subregions has less than a preselected concentration, at least one of, decreasing an exhaust rate of the deactivation gas from the subregion, and directing the decontamination gas to the corresponding subregion from neighboring subregions; and, continuing to introduce and circulate the deactivation gas until any biological or chemical agents in the space are deactivated.

2. The method according to claim 1, wherein controlling the circulation of the decontamination gas from subregion to adjoining subregion includes controlling each of a plurality of circulation fans which move the decontamination gas from one of the subregions to an adjoining subregion.

3. The method according to claim 2, further including:

exhausting air, spent deactivation gas, and deactivation gas from the space; and, trapping any entrained biological or chemical agent in the exhausted air, spent deactivation gas, and deactivation gas.

4. The method according to claim 3 further including: before introducing the deactivation gas, exhausting to bring the space at a negative pressure.

5. The method according to claim 1, further including:

sensing temperature at a plurality of locations around the space and in each of the subregions; and, wherein the preselected maximum concentration in each subregion is a saturation or condensation concentration at the sensed temperature in the subregion.

6. The method according to claim 1, wherein the sensing includes:
altering a resonance frequency, a capacitance, or other electrical property of a sensing element with the deactivation gas.

7. The method according to claim 1 wherein the deactivation gas includes hydrogen peroxide vapor.

8. The method according to claim 1 wherein introducing the deactivation gas includes:
vaporizing a liquid deactivation concentrate to generate the deactivation gas.

9. The method according to claim 8 wherein the vaporizing step is performed by one or more of:
at a plurality of generators built into the space;
at portable generators movably placed within the space.

10. The method according to claim 1 further including:
with a computer processor, controlling the introduction and circulation of the deactivation gas into and between the subregions such that the concentration of the decontamination gas throughout the space is maintained above a preselected minimum concentration and below a preselected maximum concentration in each subregion.

11. The method as set forth in claim 1, wherein the preselected maximum concentration is a saturation or condensation concentration at the sensed temperature.

12. The method according to claim 1, further including:
automatically closing doors to isolate the space from the environment before introducing the deactivation gas.

13. The method according to claim 1, wherein the space is an elongated space and includes multiple interconnected floors with a free flow of air between floors.

14. The method according to claim 13, wherein the space includes an airport concourse.

15. The method according to claim 13, wherein the space includes a wing of a building including corridors, individual offices or rooms, cubicles, or laboratories.

16. The method according to claim 13, wherein the circulating step includes:
controlling a speed and orientation of a plurality of fans to move the deactivation gas between the subregions to maintain a concentration of the deactivation gas between a preselected minimum and a preselected maximum throughout the space.

17. The method as set forth in claim 1, wherein each of the sensors includes:
an electrical element whose electrical properties are altered in accordance with at least concentration of the deactivation gas.

18. The method according to claim 17 wherein the sensor includes:
a pair of capacitive plates between which deactivation gas is passed such that a dielectric constant of the space between the dielectric plates varies in accordance with a concentration of the deactivation gas.

19. The method according to claim 17 wherein the sensor includes:
a resonator whose resonance frequency changes in accordance with a concentration of the deactivation gas.

20. The method according to claim 1, wherein the sensing step includes:
passing the decontamination gas over a coating on at least one surface of a piezoelectric resonator having a characteristic resonance frequency, which coating interacts with the deactivation gas and changes the resonance frequency of the resonator in accordance with a concentration of the deactivation gas;
determining the concentration of the deactivation gas from the changed resonance frequency.

21. The method as set forth in claim 1, wherein the flow dynamics modeling includes taking into account interactions between subregions of a hermetically sealed zone defined by a plurality of subregions.

22. The method as set forth in claim 1, wherein the flow dynamics modeling includes redirecting circulation to accelerate dispersal of the decontamination gas from subregions with higher concentrations to subregions with lower concentrations.

23. A method of deactivating biological or chemical agents in a large volume isolated space having a plurality of subregions which are physically interconnected with a convoluted configuration, the method comprising:

isolating the space;

introducing a deactivation gas into the plurality of subregions of the isolated space;

circulating the deactivation gas within each subregion and from subregion to adjoining subregions;

continuing to introduce and circulate the deactivation gas until any biological or chemical agents in the space are deactivated;

exhausting air, spent deactivation gas, and deactivation gas from the space;

trapping any entrained biological or chemical agent in the exhausted air, spent deactivation gas, and deactivation gas;

employing a plurality of fans for exhausting the air, spent deactivation gas, and deactivation gas at a plurality of locations within the isolated space and for circulating the deactivation gas among the subregions; and with a computer, controlling the fans using flow dynamics modeling to control flow of the deactivation gas among the subregions including:

in response to a concentration of the deactivation gas in one subregion approaching a saturation level or a condensation point, controlling the fans to increase a flow of the deactivationg gas from the one subregion to neighboring subregions, and in response to the concentration in the subregion falling below a selected minimum, directing the decontamination gas to the one subregion from neighboring subregions.

24. The method according to claim 23, wherein the deactivation gas includes hydrogen peroxide vapor.

25. The method according to claim 23, wherein introducing the deactivation gas includes:
vaporizing a liquid deactivation concentrate to generate the deactivation gas.

26. The method according to claim 25, wherein the vaporizing step includes one of:
vaporizing the concentrate within an HVAC system for heating and cooling the space;
vaporizing the concentrate with a plurality of vaporizers built into the space;
vaporizing the concentrate in portable generators movably placed within the space.

27. A method of deactivating biological or chemical agents in a large volume space with a plurality of fluidly interconnected subregions among which subregions air flows freely, the method comprising:
isolating the space;
with a computer, monitoring each of a plurality of deactivation gas concentration sensors around the space;
with the computer, performing flow dynamic modeling routine;
with the computer, controlling deactivation gas generator in accordance with the flow dynamics modeling routine to control a distribution of a deactivation gas among the subregions including:
in response to the sensors sensing that a concentration in one or more high concentration subregions is approaching a saturation level or a condensation point, reducing a supply of the deactivation gas to the high concentration subregions and drawing the deactivation gas from the high concentration subregions to other subregions, and
in response to the sensors sensing that the concentration in one or more low concentration subregions is approaching a selected minimum concentration, increasing the supply of the deactivationg gas to the low concentration subregions and drawing decontamination gas from other subregions into the low concentration subregion.

28. The method according to claim 27, further including:
controlling fans to exhaust air, spent deactivation gas, and deactivation gas from the space;
trapping entrained biological or chemical agent in the exhausted air, spent deactivation gas, and deactivation gas.

* * * * *